United States Patent [19]

Croquevielle

[11] Patent Number: 5,342,329
[45] Date of Patent: Aug. 30, 1994

[54] PORTABLE DISPOSABLE DEVICE FOR POST-SURGICAL SUCTION

[75] Inventor: Raul J. Croquevielle, Santiago, Chile

[73] Assignee: Inmed Ltda., Chile

[21] Appl. No.: 946,943

[22] Filed: Sep. 17, 1992

[30] Foreign Application Priority Data

Oct. 11, 1991 [CL]  Chile ........................ 978-91

[51] Int. Cl.⁵ ............................................. A61M 1/00
[52] U.S. Cl. .................................. 604/319; 128/766; 604/118; 604/213; 604/247
[58] Field of Search ............... 604/73, 212, 213, 216, 604/210, 319, 118, 247; 128/749, 752, 758, 765, 766

[56] References Cited

U.S. PATENT DOCUMENTS

| | | | |
|---|---|---|---|
| 991,022 | 5/1911 | Rees et al. | 604/212 |
| 3,683,929 | 8/1972 | Holter | 604/212 |
| 3,752,146 | 8/1973 | Kline | 128/749 |
| 4,068,662 | 1/1978 | Sneider | 604/216 |
| 4,392,860 | 7/1983 | Huck et al. | 604/212 |
| 4,402,687 | 9/1983 | Denty et al. | 604/319 |
| 4,460,354 | 7/1984 | Weilbacher et al. | 604/73 |
| 4,551,141 | 11/1985 | McNeil et al. | 604/319 |
| 4,573,992 | 3/1986 | Marx | 604/319 |
| 4,642,088 | 2/1987 | Günter | 604/216 |
| 4,828,546 | 5/1989 | McNeil et al. | 604/213 |
| 4,921,488 | 5/1990 | Martz et al. | 604/319 |
| 5,002,529 | 3/1991 | Cunningham | 604/73 |
| 5,102,404 | 4/1992 | Goldberg et al. | 604/317 |
| 5,141,503 | 8/1992 | Sewell, Jr. | 604/317 |

FOREIGN PATENT DOCUMENTS

| | | | |
|---|---|---|---|
| 1316596 | 12/1962 | France | 604/212 |
| 854397 | 11/1979 | U.S.S.R. | 604/319 |
| 1398873 | 5/1988 | U.S.S.R. | 604/319 |
| 9003194 | 4/1990 | World Int. Prop. O. | 604/319 |

OTHER PUBLICATIONS

Promotional materials for Hemo Suc (TM) suction unit.

Primary Examiner—Randall L. Green
Assistant Examiner—Rob Clarke
Attorney, Agent, or Firm—Donald Brown; Peter F. Corless

[57] ABSTRACT

A portable, closed circuit, disposable device for post operatory surgical suction which comprised a bellows-shaped body receptacle for suctioned fluids, a threaded neck located on the upper surface of said bellows-shaped body suitable to receive a threaded cap; said cap being provided with a suction tube system connected through said cap into the bellows-shaped body, and said system of tubes is provided with a check-valve, wherein said bellows-shaped body is provided with a cannula in its lower surface, having a nearly rectangular longitudinal section, having a lower end wall, wherein the side wall of said cannula is provided with at least one opening located in a position close to said lower end wall of said cannula; where an elastic tube, with a longer extension than said cannula, is introduced under pressure in said cannula in order to close the at least one opening of said cannula, and wherein a tube of rigid or semi-rigid material is introduced in said cannula, fixing the elastic tube between its interior side wall and the exterior side wall of said cannula.

9 Claims, 1 Drawing Sheet

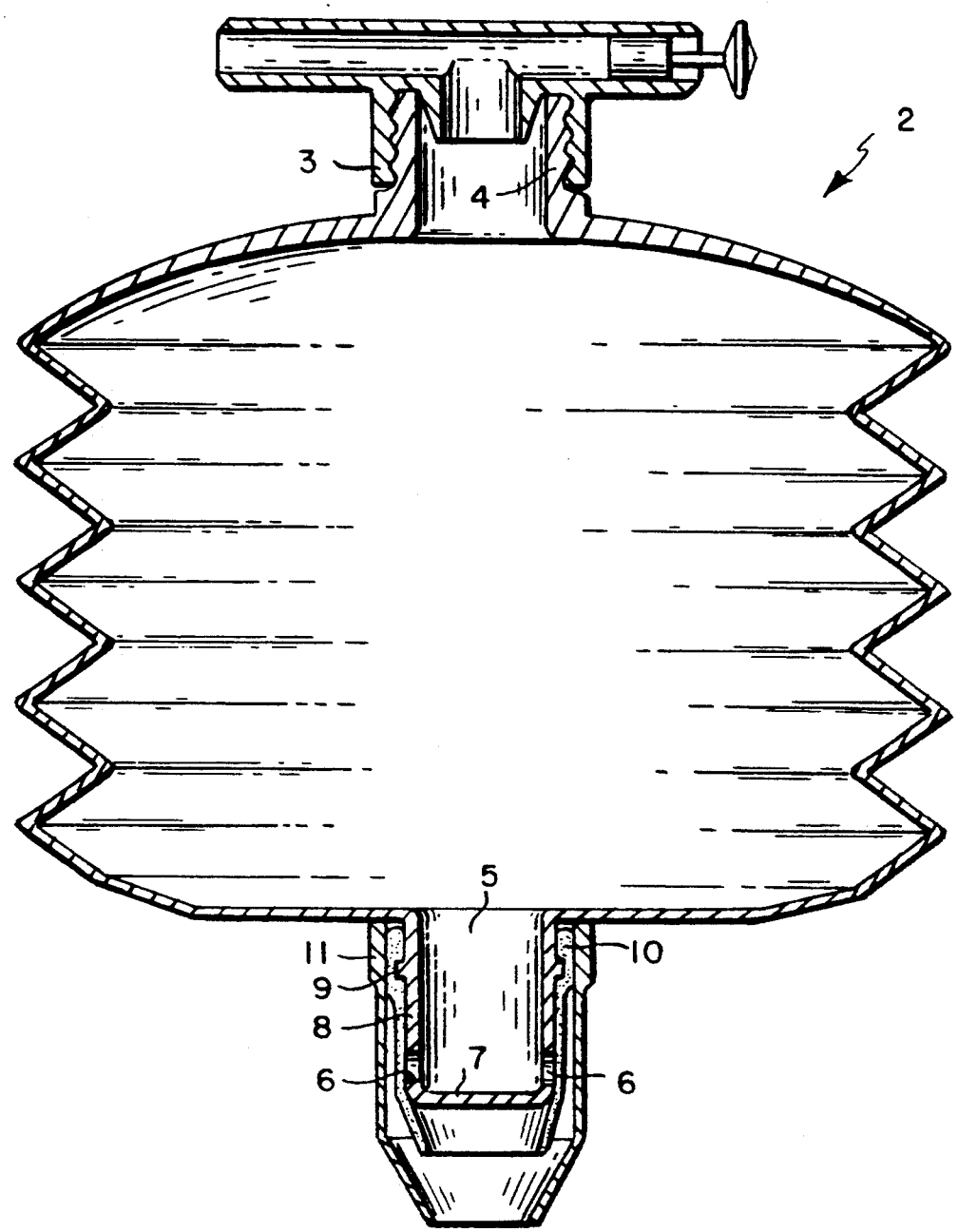

PORTABLE DISPOSABLE DEVICE FOR POST-SURGICAL SUCTION

TECHNICAL FIELD

The present invention relates to a portable disposable device for post operatory surgical suction comprising a novel draining system; and more specifically, it relates to a closed circuit, post-surgical suction device comprising a drainage cannula which impedes potential contamination of the operator.

BACKGROUND OF THE INVENTION

Known post operatory suction devices are based on a bellows-shaped body, which acts as the suction receptacle, normally provided with a threaded neck on its upper surface, said neck being apt to receive a threaded cap; wherein said cover is equipped with a system of suction tubes or pipes connected through said cover with the inside of said bellows-shaped body; said tube system being provided with a check valve, and since the system is sealed, when the bellows-shaped body is collapsed an internal negative pressure is generated in the interior of the bellows-shaped body providing suction capacity therein. The suction capacity will operate from the injury, through the tubes, and up to the bellows-shaped body where the suctioned liquids are deposited. Once the bellows-shaped body has recovered its maximum extended capacity, the device loses its suction capacity and the same contains the aspirated or suctioned liquids. It is then necessary to open the system—by separating the body from the tube system—in order to be able to empty the contents of said bellow-shaped body to a waste matter container. The device is provided with two access ports: a first port connected to the tube or tubes directed to the injury, through which tubes the fluids are drained to the inside of the device; and a second port provided with a cap or a plug, which may have various shapes depending on the specific design, for drainage of liquids suctioned cut of the wound.

Thus, the state-of-the art equipment presents two risk factors, namely: a) when the equipment is opened, the normal contaminating elements present in a post-operatory room, can penetrate into the collector device and, through the connection of the same, they may reach the wound; and b) the operator of the equipment, independent of careful handling, is highly exposed to contamination from the extracted fluids, which certainly present risk due to viruses such as hepatitis B, AIDS, and many others.

OBJECTS OF THE INVENTION

It is an object of present invention to eliminate, or dramatically reduce, risk of contamination of the operator of such a suction device.

Another object of the invention is to permanently maintain isolation of the inside of the closed circuit; thus eliminating eventual contamination coming from the environment.

Still another object of the invention is to permit the medical and paramedical operators to empty and reactivate the system in one simple operation, by means of compressing the bellows-shaped body.

BRIEF DESCRIPTION OF THE DRAWINGS

For better description of the invention, an schematic FIGURE is furnished, illustrating a simple front view of the bellows-shaped body of the suction device of the invention, in a longitudinal cross-section.

DETAILED DESCRIPTION OF THE INVENTION

The bellows-shaped body 2 is provided with a top cover 3 located on its top surface. On the bottom surface, cannula 5 projects in the opposite direction to the neck 5, said cannula 5 having a longitudinal cross section which is preferably rectangular (or slightly conical towards the lower edge), and is provided with a bottom wall 7 that presents right angles in relation to the lateral, circular wall 8, where said cannula is provided with two or more openings 6, located as near as possible to the bottom 7 of said cannula 5. These openings 6 must be located as close as possible to the lower wall 7 in order to avoid residual materia to remain inside the bellows-shaped body 2 during the discharge operation of said bellows-shaped body 2. Lateral wall 8 of said cannula 5 may be provided with one or more rims 9 on its outer surface.

A small tube 10, which is preferably made of latex or similar elastic material, is introduced in said cannula 5. Tube 10 must be placed in position under tight pressure relation in said cannula 5, and the pressure applied by tube 10 on openings 6 of the cannula 5 must be calculated so as to permit the discharge of the accumulated liquids in the bellows-shaped body 2, under manual pressure applied by the operator while tending to join the upper and lower surfaces of the bellows-shaped body 2; thus, accumulated liquids in the interior of the body will exit through the holes 6 of cannula 5 and the tube 10. Once the emptying operation takes place, tube 10 will impede introduction of air into the bellows-shaped body 2, wherein said bellows-shaped body 2 is prepared and ready for a new suction cycle. The at least one rim 9 located on the outside of the cannula 5, permits a better attachment between the outside surface of wall 8 of cannula 5 and the interior of tube 10; naturally it is also possible to apply other means to obtain said better attachment, i.e. small protruding portions—with different shapes—, located on said outer wall of the cannula 5, or a corrugated surface of same, among others.

Finally, a protection and closure tube or cap 11, made of suitable rigid material, is placed over the cannula/elastic tube combination; said tube 11 will have a suitable interior diameter to be introduced with a predetermined pressure in contact with the assembly of the cannula and the elastic tube so as to apply an adequate pressure on the elastic tube 10 in the direction of the outside surface of cannula 5 in the contact surface between both elements except in the region where openings 5 of the cannula are located thus improving the adherence between the tube 10 and the outside wall of the cannula 5.

The discharge aperture of tube 11, which closes the device of the invention, preferably has a small diameter than rest of the tube 11, in order to direct fluids to the waste materia receptacle; in order to discharge said fluids preventing the same from coming in contact with the operator of the device.

What is claimed is:

1. A portable, closed circuit, disposable device for post operatory surgical suction comprising a bellows-shaped body receptacle for suctioned fluids, said bellows-shaped body having an upper surface and a lower surface, a threaded neck located on the upper surface of said bellows-shaped body suitable to receive a threaded cap, a suction tube system comprising a check valve connected through said cap into the bellows-shaped body, said lower surface of the bellows-shaped body comprising a cannula having a side wall and a lower end wall extending from said side wall, said side wall of said cannula being provided with at least one opening located in a position proximate to said lower end wall of said cannula, and wherein an elastic tube, with a longer extension than said cannula, is placed in said cannula to thereby close the at least one opening of said cannula, and wherein a tube of rigid or semi-rigid material is placed on said cannula.

2. The device of claim 1 wherein said cannula has a transverse conical section proximate to said lower end wall, and said side wall and lower end wall of the cannula being joined to form an angle within the cannula of about 90° or wider.

3. The device of claims 1 or 2 wherein the bellows-shaped body receptacle comprises liquid and pressure applied by the tube in the cannula over the at least one opening of said cannula is calculated so that said tube permits flow of the liquid from the bellows-shaped body.

4. The device of claim 1 wherein the cannula has an outer surface in contact with the elastic tube, and said outer surface of the cannula has one or more peripheral rims.

5. The device of claim 1 wherein the cannula has an outer surface in contact with the elastic tube, and said outer surface of the cannula comprises projections.

6. The device of claim 1 wherein the cannula has an outer surface in contact with the elastic tube, and said outer surface of the cannula comprises a substantially corrugated surface.

7. The device of claim 1 wherein the cannula has an outer surface in contact with the elastic tube, and said outer surface of the cannula comprises both projections and a substantially corrugated surface.

8. The device of claim 1 wherein said elastic tube is formed from a latex material.

9. The device of claim 1 wherein a surface of the cannula contacts the elastic tube, and said rigid tube has an interior diameter suitable to enter, at a predetermined pressure, in contact with the cannula and elastic tube combination to exert pressure on said elastic tube in the direction of the surface of the cannula that contacts the elastic tube except in the region where said at least one hole of the cannula is located, wherein in said region the lower end of the rigid tube has a reduced diameter.

* * * * *